(12) United States Patent
Li et al.

(10) Patent No.: US 11,812,551 B2
(45) Date of Patent: Nov. 7, 2023

(54) FLEXIBLE CIRCUIT BOARDS FOR CONTINUOUS ANALYTE MONITORING DEVICES

(71) Applicant: Ascensia Diabetes Care Holdings AG, Basel (CH)

(72) Inventors: Ji Li, Wayne, NJ (US); Igor Y. Gofman, Croton-on-Hudson, NY (US); Dragan Avirovikj, Stamford, CT (US); Thomas A. J. Mayer, Jr., Glenmoore, PA (US); Cameron M. Young, Tarrytown, NY (US); Nicholas Erekovcanski, Butler, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 7 days.

(21) Appl. No.: 17/562,920

(22) Filed: Dec. 27, 2021

(65) Prior Publication Data

US 2022/0210907 A1     Jun. 30, 2022

Related U.S. Application Data

(60) Provisional application No. 63/131,273, filed on Dec. 28, 2020.

(51) Int. Cl.
  *H05K 1/02* (2006.01)
  *H05K 1/11* (2006.01)
  *H05K 3/36* (2006.01)

(52) U.S. Cl.
  CPC ............. *H05K 1/028* (2013.01); *H05K 1/118* (2013.01); *H05K 3/361* (2013.01)

(58) Field of Classification Search
  CPC ......... H05K 1/028; H05K 1/118; H05K 3/361
  USPC ......................................................... 174/254
  See application file for complete search history.

(56) References Cited

U.S. PATENT DOCUMENTS

| | | |
|---|---|---|
| 9,380,698 B1 | 6/2016 | Li et al. |
| 9,801,270 B2 | 10/2017 | Tuominen et al. |
| 11,395,608 B2 | 7/2022 | Kube et al. |

(Continued)

FOREIGN PATENT DOCUMENTS

CN     1166893 A  * 12/1997  ............. H01R 12/79

OTHER PUBLICATIONS

WIPO Application No. PCT/EP2021/087700, International Search Report and Written Opinion of the International Searching Authority, dated Mar. 29, 2022.

(Continued)

*Primary Examiner* — Andargie M Aychillhum
(74) *Attorney, Agent, or Firm* — ERISE IP, P.A.

(57) ABSTRACT

A flexible circuit board for a continuous analyte monitoring (CAM) device includes a plurality of physically separate circuit board cells each having circuitry thereon. The flexible circuit board also includes a plurality of flexible interconnections each connecting one of the physically separate circuit board cells to another of the physically separate circuit board cells. Each one of the flexible interconnections is operable to couple power, electrical signals, or both to the physically separate circuit board cells connected thereto. The flexible circuit board is bendable in multiple directions in three dimensions. Methods of constructing flexible circuit boards for CAM devices are also provided, as are other aspects.

20 Claims, 7 Drawing Sheets

(56) References Cited

U.S. PATENT DOCUMENTS

| | | | | |
|---|---|---|---|---|
| 2015/0327359 A1* | 11/2015 | Tuominen | ................. | H01P 3/08 |
| | | | | 333/238 |
| 2016/0165719 A1* | 6/2016 | Li | ............................ | H05K 3/30 |
| | | | | 361/749 |
| 2016/0317057 A1* | 11/2016 | Li | ........................ | A61B 5/6833 |
| 2017/0367172 A1 | 12/2017 | Yee et al. | | |
| 2018/0014783 A1* | 1/2018 | Shi | ......................... | A61B 5/259 |
| 2020/0046270 A1 | 2/2020 | Kube et al. | | |
| 2020/0218364 A1* | 7/2020 | Kim | ......................... | G06F 3/038 |
| 2020/0249773 A1* | 8/2020 | Lee | ......................... | G06F 3/038 |

OTHER PUBLICATIONS

PCT Patent Application PCT/EP2021/087700 Written Opinion of the International Preliminary Examining Authority dated Dec. 12, 2022.

PCT Patent Application PCT/EP2021/087700 The International Preliminary Report on Patentability dated Mar. 30, 2023.

* cited by examiner

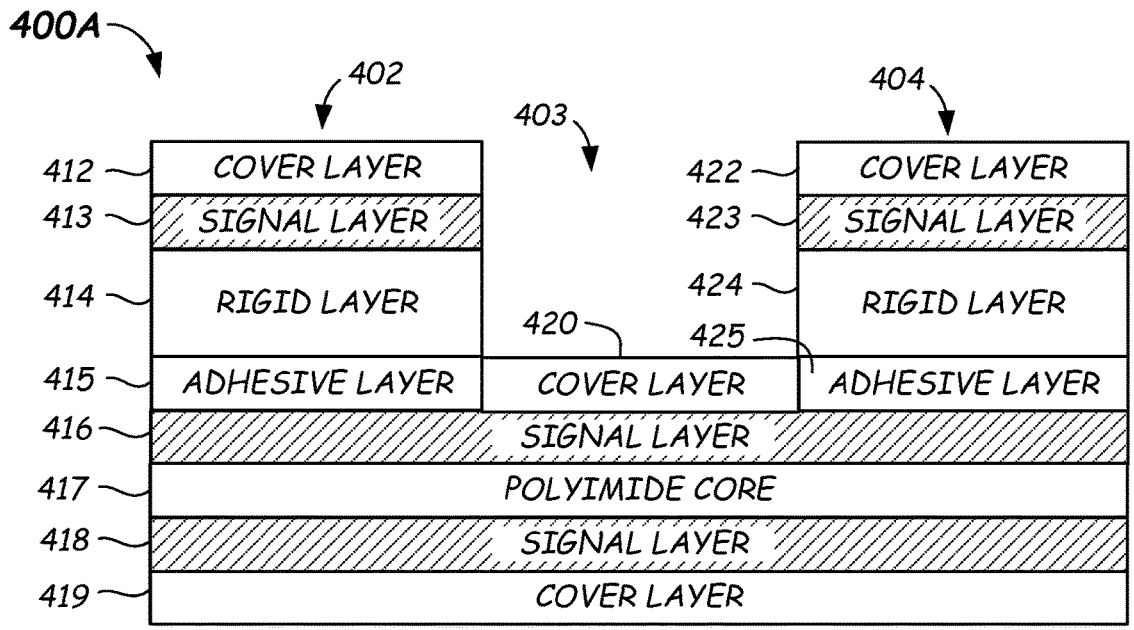
FIG. 4A
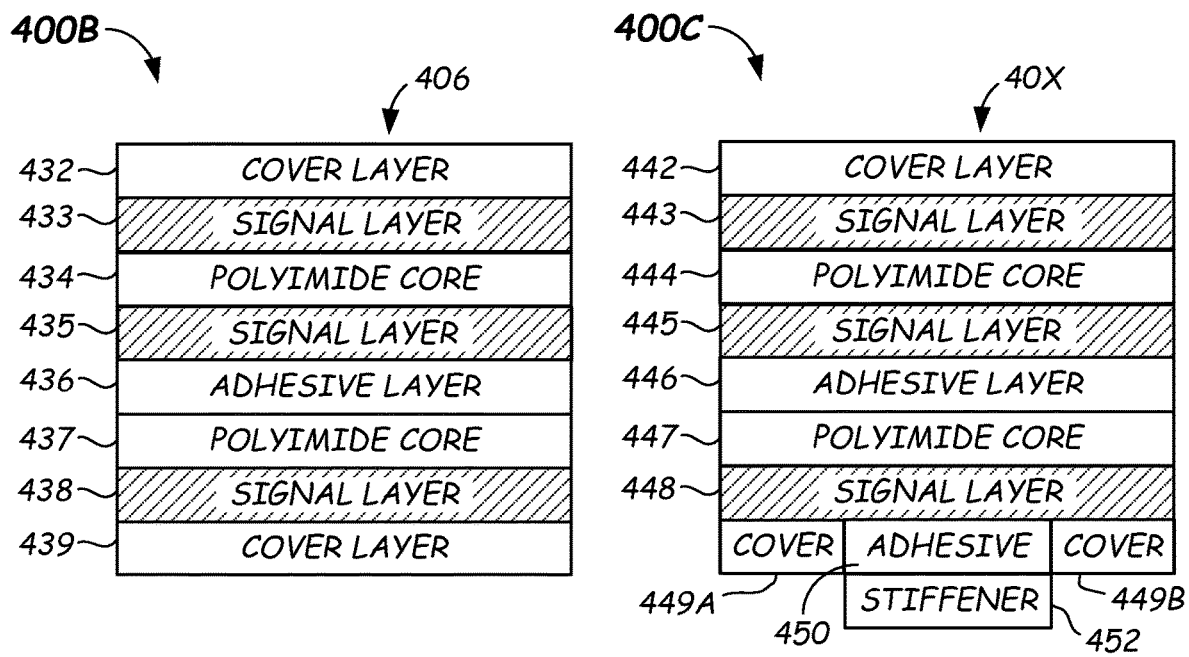
FIG. 4B
FIG. 4C

FLEXIBLE CIRCUIT BOARDS FOR CONTINUOUS ANALYTE MONITORING DEVICES

CROSS REFERENCE TO RELATED APPLICATION

This claims the benefit of U.S. Provisional Patent Application No. 63/131,273, filed Dec. 28, 2020, the disclosure of which is hereby incorporated by reference herein in its entirety for all purposes.

FIELD

The present disclosure relates to flexible circuit boards for continuous analyte monitoring devices.

BACKGROUND

Continuous analyte monitoring (CAM), such as continuous glucose monitoring (CGM), has become a routine monitoring operation, particularly for individuals with diabetes. By providing real-time analyte (e.g., glucose) readings, therapeutic actions may be taken in a timelier fashion and, in the case of CGM, a glycemic condition may be better controlled. A sensor of a CAM device is typically inserted subcutaneously into a user, while the CAM device adheres to an outer surface of the user's skin, such as on the abdomen or back of the upper arm. The CAM device is continuously operated in that the sensor provides signals to a wireless transmitter of the CAM device. The signals are indicative of the user's analyte (e.g., glucose) level. A handheld CAM receiver (e.g., a smartphone) may process the signals received from the CAM device and display analyte readings. Analyte readings may be provided automatically many times throughout the day (e.g., every few minutes or at some other pre-established time interval).

A CAM device may include a flexible circuit board, which is an assembly of electronic circuits and components (referred to hereinafter as "circuitry") fabricated on a flexible substrate. Flexible circuit boards are intended to allow a CAM device to conform to a user's skin surface and, ideally, conform to the skin surface while the user moves about. However, the degree of flexibility and/or the directions in which known flexible circuit boards can bend may be limited, thus adversely affecting the wearing comfort and adherence of the CAM device to and on the user's skin surface.

Improved flexible circuit boards for CAM devices are accordingly desired.

SUMMARY

In some embodiments, a flexible circuit board for a continuous analyte monitoring (CAM) device is provided that includes a plurality of physically separate circuit board cells each having circuitry thereon. The flexible circuit board also includes a plurality of flexible interconnections each connecting one of the plurality of physically separate circuit board cells to another of the plurality of physically separate circuit board cells. Each one of the plurality of flexible interconnections is operable to couple power, electrical signals, or both to physically separate circuit board cells connected thereto. The flexible circuit board is bendable in multiple directions in three dimensions.

In some embodiments, a method of constructing a flexible circuit board for a continuous analyte monitoring (CAM) device is provided. The method includes providing a plurality of physically separate circuit board cells each having circuitry thereon and interconnecting each one of the plurality of physically separate circuit board cells to another of the plurality of physically separate circuit board cells with a respective flexible interconnection operable to couple power, electrical signals, or both to the one and the another of the plurality of physically separate circuit board cells.

Still other aspects, features, and advantages of this disclosure may be readily apparent from the following detailed description and illustration of a number of example embodiments and implementations, including the best mode contemplated for carrying out the invention. This disclosure may also be capable of other and different embodiments, and its several details may be modified in various respects, all without departing from the scope of the invention. For example, although the description below relates to CAM and CGM devices, the flexible circuit boards described below may be readily adapted to other electronic devices, particularly miniature user wearable electronic devices, that would benefit from circuit boards having increased flexibility. This disclosure is intended to cover all modifications, equivalents, and alternatives falling within the scope of the appended claims (see further below).

BRIEF DESCRIPTION OF DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

FIGS. 4A, 4B, and 4C illustrate cross-sectional side views of layer stacks of flexible circuit board components according to embodiments provided herein.

DETAILED DESCRIPTION

Embodiments described herein provide a continuous analyte monitoring (CAM) device that can be comfortably worn on and attached to a user's body (e.g., the abdomen, upper arm, or other suitable location). The CAM device includes an assembly of electronic circuits and components, which may be in the form of printed circuits and individual electronic components (referred to collectively hereinafter as "circuitry") that perform analyte monitoring. The CAM circuitry is fabricated on a highly flexible circuit board. The highly flexible circuit board is advantageously partitioned into small, relatively physically independent circuit board cells interconnected with flexible interconnections that provide improved flexibility of the CAM device in multiple directions, thus improving the comfort of the CAM device while worn on the user.

Advantageously, a CAM device constructed with the highly flexible circuit board can be attached to a user's body without regard to orientation of the device. That is, the omnidirectional flexibility of the CAM device provided by the highly flexible circuit board negates the need to follow any particular contour of the skin when positioning and attaching the CAM device to the user's body.

Each circuit board cell has circuitry fabricated thereon. The circuit board cells are interconnected to each other with flexible interconnections. The flexible interconnections are configured to provide electrical signals and power to interconnected circuit board cells. In some embodiments, the flexible interconnections may also be fabricated with circuitry thereon supported where needed by stiffeners applied to the flexible interconnections. In some embodiments, one or more circuit board cells and flexible interconnections may be a High Density Interconnect (HDI) component.

Each circuit board cell may be constructed with an ultra-thin layer stack, which may include three signal layers. One or more signal layers may have a hatched ground plane instead of a solid conductor ground plane. The hatched ground plane contributes further to increased flexibility. In some embodiments, the layer stack may have a total thickness of only about 6.5 mils (about 0.17 mm). This advantageously results in highly flexible and ultra-low profile CAM devices that may reduce interference with clothing, be more discreet, and improve overall wearing comfort through a range of motions by a user.

In accordance with one or more embodiments, highly flexible circuit boards and methods of their construction, and devices and systems including such circuit boards, are provided herein, as will be explained in greater detail below in connection with FIGS. 1-7.

Figure 1:
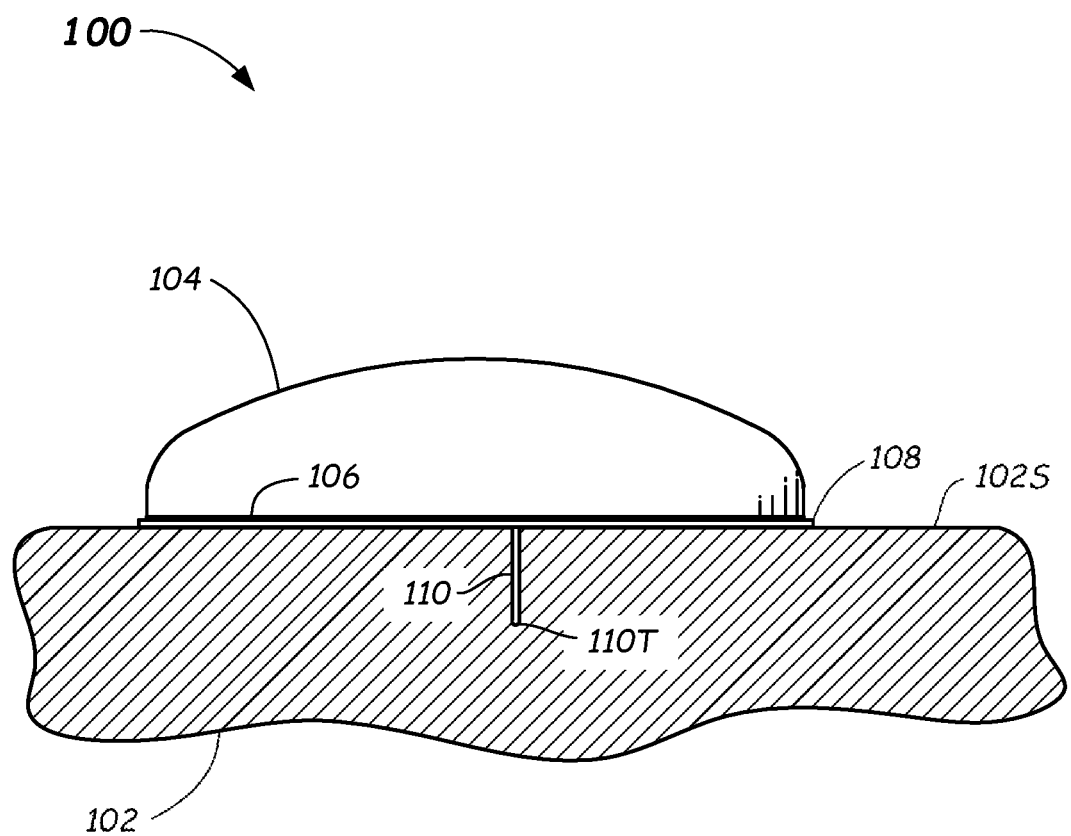
FIG. 1 illustrates a side elevation view of a continuous glucose monitoring (CGM) device that includes sensor circuitry and wireless communication circuitry according to embodiments provided herein.

FIG. 1 illustrates a wearable continuous glucose monitoring (CGM) device 100, which is an example of a CAM device, according to one or more embodiments. As shown, CGM device 100 may be attached (via an adhesive) to the skin 102 of a user. CGM devices, systems, and methods typically generate electrochemical glucose signals continuously during operation and perform glucose measurements/ estimations based on the generated signals typically every few minutes. That is, CGM device 100 is configured to continuously monitor and provide periodic glucose readings (e.g., every 5 minutes or other suitable time interval). CGM device 100 may include a housing 104 that may enclose sensor circuitry and wireless communication circuitry therein (neither shown in FIG. 1). Housing 104 may include a flexible base 106 and an adhesive layer 108, which may be, e.g., a double-sided tape or pressure sensitive adhesive. One side of adhesive layer 108 may adhere to flexible base 106, while the other side of adhesive layer 108 may adhere to skin surface 102S of the user. Although shown as partially dome shaped, housing 104 may be of other suitable shapes.

The sensor circuitry of CGM device 100 may include a sensor 110, a portion of which is shown inserted through the user's skin 102. Sensor 110 may extend from the sensor circuitry through flexible base 106 and may be configured to be at least partially located in interstitial fluid in a subcutaneous region of a user. Sensor 110 may be or may include an analyte sensor or an analyte sensor portion, such as at or near a sensor tip 110T. Sensor 110 may be inserted with an insertion device (not shown) having a sharpened needle or "introducer" that pierces the skin to introduce sensor 110 into a subcutaneous region of a user.

The wireless communication circuitry of CGM device 100 may include one or more electronic components that communicate with the sensor circuitry and with one or more external devices (e.g., a hand-held CGM receiver or other portable device, such as a smartphone executing a suitable CGM application software program) to provide glucose measurement signals and/or measurement results.

Figure 2A:
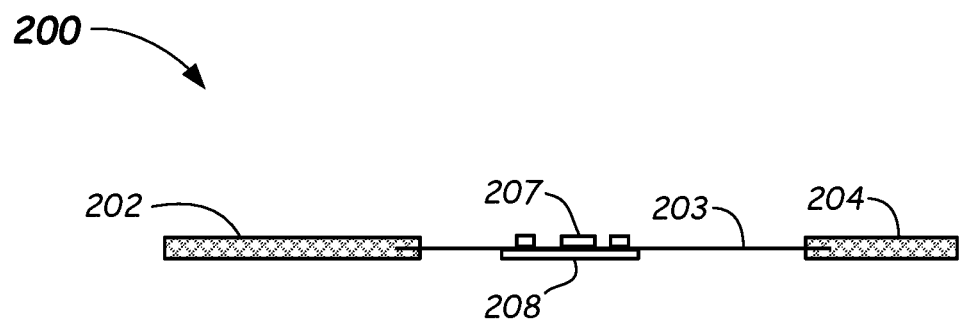
FIGS. 2A and 2B illustrate (top) side and plan views, respectively, of a flexible circuit board configuration according to embodiments provided herein.
Figure 2B:
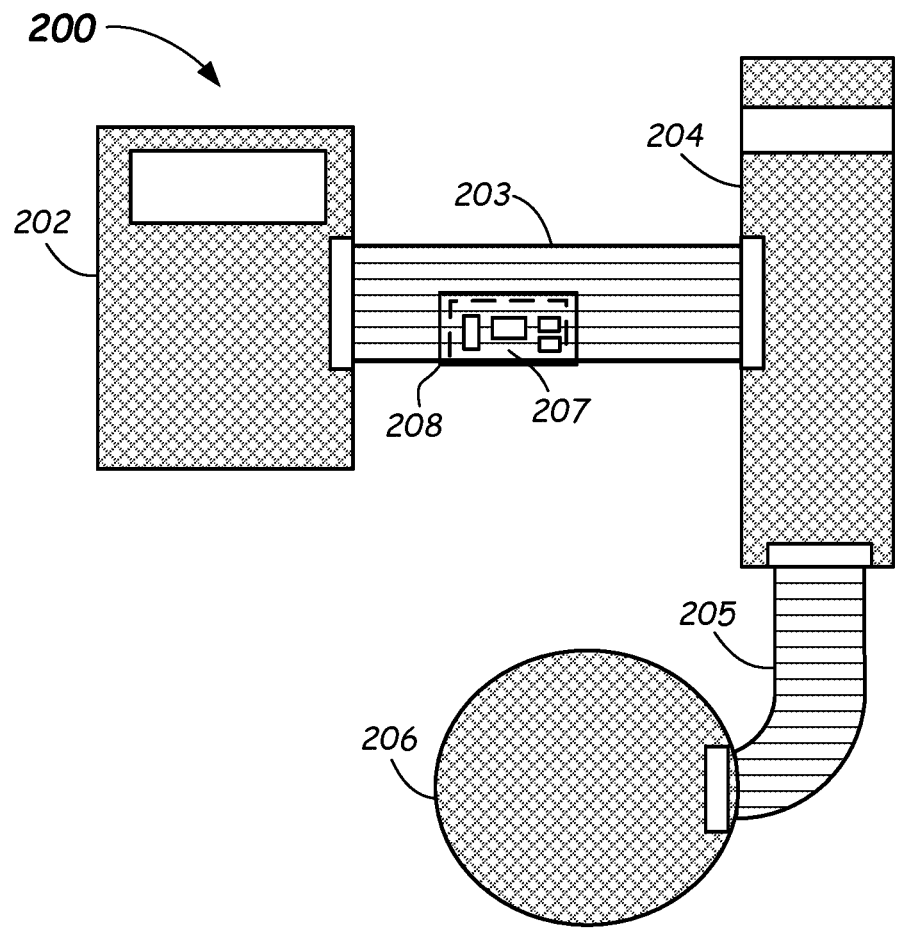

FIGS. 2A and 2B illustrate a highly flexible circuit board configuration 200 that may be fabricated to include, e.g., the sensor circuitry and wireless communication circuitry of CGM 100 according to one or more embodiments. Other circuitries may instead be fabricated thereon. Flexible circuit board configuration 200 may include circuit board cells 202, 204, and 206 and flexible interconnections 203 and 205. Circuit board cell 202 is interconnected to circuit board cell 204 via flexible interconnection 203, and circuit board cell 204 is interconnected to circuit board cell 206 via flexible interconnection 205. Flexible interconnection 203 is configured to connect electrical signals and power between circuit board cells 202 and 204, and flexible interconnection 205 is configured to connect electrical signals and power between circuit board cells 204 and 206. As shown, circuit board cells 202, 204, and 206 and flexible interconnections 203 and 205 are not limited to any specific size or any particular shape. In other embodiments, flexible circuit board configuration 200 may have other numbers of circuit board cells and flexible interconnections.

Flexible interconnections 203 and 205 are each fixedly and/or permanently attached to (in any suitable manner) and/or integrally formed with circuit board cells 202, 204, and 206 during a flexible circuit board manufacturing process. Flexible interconnections 203 and 205 are not detachable connectors configured to be removable and reconnectable as commonly used to connect printed circuit boards in larger electronic devices.

In some embodiments, a flexible interconnection, such as, e.g., flexible interconnection 203, may have circuitry 207 fabricated thereon, which may be supported by a stiffener 208 applied to flexible interconnection 203. Stiffener 208 may be applied to a side of flexible interconnection 203 opposite the side upon which circuitry 207 is fabricated.

The materials and layer stacks that may be used to construct one or more of circuit board cells 202, 204, and 206 and/or flexible interconnections 203 and 205 are described below in connection with FIGS. 4A-C.

Figure 3:
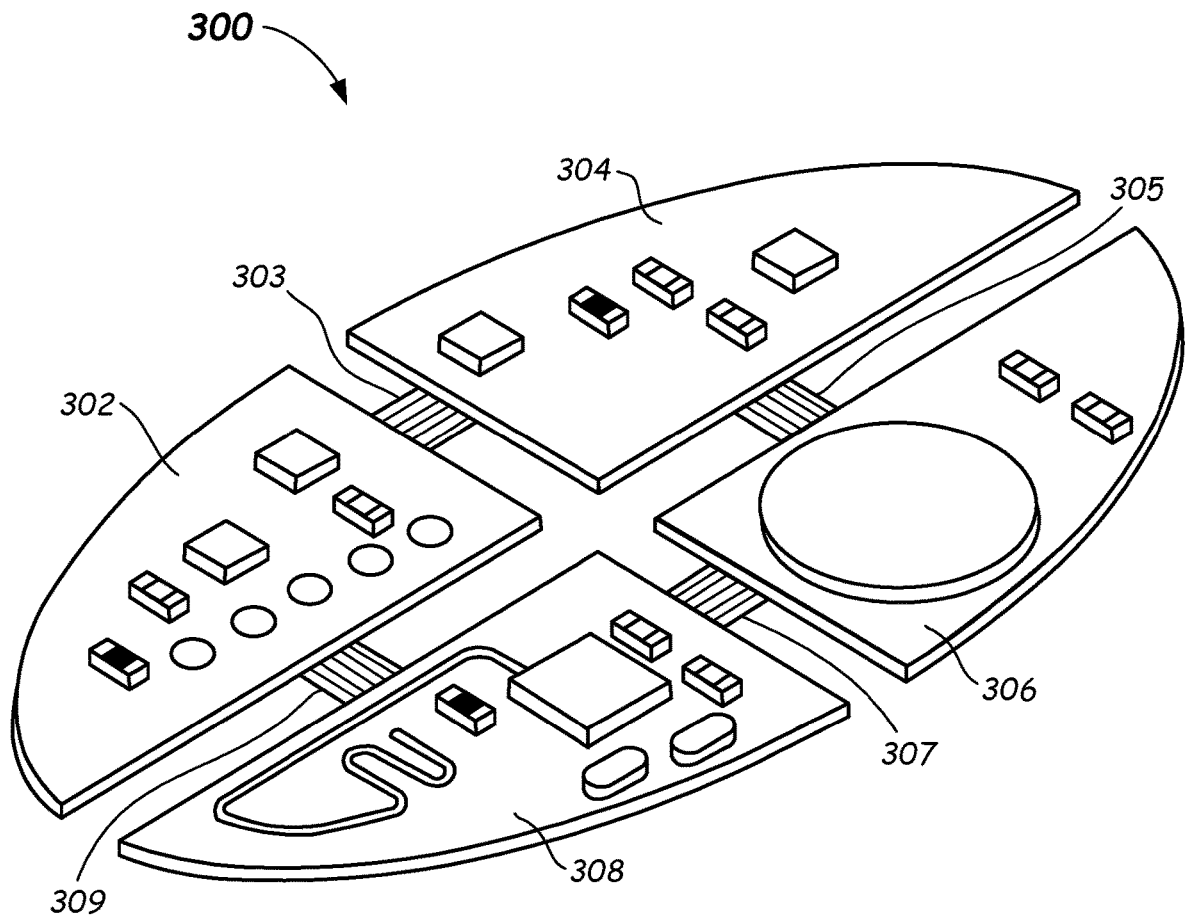
FIG. 3 illustrates a perspective view of another flexible circuit board configuration according to embodiments provided herein.

FIG. 3 illustrates another highly flexible circuit board configuration 300 that may be fabricated to include, e.g., the sensor circuitry and wireless communication circuitry of CGM 100 according to one or more embodiments. Other circuitries may instead be fabricated thereon. Flexible circuit board 300 may include circuit board cells 302, 304, 306, and 308 and flexible interconnections 303, 305, 307, and 309. As shown, circuit board cell 302 is interconnected to circuit board cell 304 via flexible interconnection 303, circuit board cell 304 is interconnected to circuit board cell 306 via flexible interconnection 305, circuit board cell 306 is interconnected to circuit board cell 308 via flexible interconnection 307, and circuit board cell 308 is interconnected to circuit board cell 302 via flexible interconnection 309. Flexible interconnection 303 is configured to connect electrical signals and power between circuit board cells 302 and 304, flexible interconnection 305 is configured to connect electrical signals and power between circuit board cells 304 and 306, flexible interconnection 307 is configured to connect electrical signals and power between circuit board cells 306 and 308, and flexible interconnection 309 is configured to connect electrical signals and power between circuit board cells 308 and 302.

Flexible interconnections 303, 305, 307, and 309 are each fixedly and/or permanently attached to (in any suitable manner) and/or integrally formed with circuit board cells 302, 304, 306, and 308 during a flexible circuit board manufacturing process. Flexible interconnections 303, 305, 307, and 309 are not detachable connectors configured to be removable and reconnectable as commonly used to connect printed circuit boards in larger electronic devices.

In some embodiments, circuitry fabricated on circuit board cells and flexible interconnections may be configured to perform CAM (or in particular CGM) and may be partitioned as follows: circuit board cell 302 may have sensor circuitry fabricated thereon, circuit board cell 304 may have interconnection circuitry fabricated thereon, circuit board cell 306 may have power circuitry and a power source fabricated thereon, and circuit board cell 308 may have wireless communication circuitry fabricated thereon. Other suitable circuitry partitioning may also be implemented.

In some embodiments, any one or more of flexible interconnections 303, 305, 307, and/or 309 may have circuitry fabricated thereon, which may be supported by a stiffener applied to the flexible interconnection, as shown in FIGS. 2A and 2B for flexible interconnection 203.

Although flexible circuit board configuration 300 is shown configured and arranged to form a generally oval shape, other suitable shapes may be formed with circuit board cells and flexible interconnections, thus advantageously allowing for customized use in, e.g., uniquely or oddly shaped devices.

In other embodiments, flexible circuit board configuration 300 may have other numbers of circuit board cells and flexible interconnections.

The materials and layer stacks that may be used to construct one or more of circuit board cells 302, 304, 306, and 308 and/or flexible interconnections 303, 305, 307, and 309 are described below in connection with FIGS. 4A-C.

The spacing between circuit board cells 202 and 204 and between circuit board cells 302, 304, 306, and 308 advantageously provides significantly increased circuit board flexibility in practically any direction in a two-dimensional plane, as described in more detail below in connection with FIGS. 6A-C.

Moreover, the cellular circuit board configurations may result in less material usage, which advantageously reduces flexible circuit board fabrication costs.

FIGS. 4A, 4B, and 4C illustrate layer stacks 400A, 400B, and 400C that can be used to construct circuit board cells and/or flexible interconnections according to one or more embodiments. The density of circuitry fabricated on a circuit board and/or a flexible interconnection and/or the number of signal lines needed between circuit board cells may determine which of layer stacks 400A, 400B, and 400C is used to construct a circuit board cell and/or flexible interconnection.

FIG. 4A illustrates the construction of circuit board cells 402 and 404 and flexible interconnection 403 using layer stack 400A. Circuit board cell 402 constructed with layer stack 400A may include cover layers 412 and 419; three signal layers 413, 416, and 418; a rigid layer 414; an adhesive layer 415; and a polyimide core 417 arranged as shown. Flexible interconnection 403 constructed with layer stack 400A may include cover layers 420 and 419; two signal layers 416 and 418; and a polyimide core 417 arranged as shown. And circuit board cell 404 constructed with layer stack 400A may include cover layers 422 and 419; three signal layers 423, 416, and 418; a rigid layer 424; an adhesive layer 425; and polyimide core 417 arranged as shown. Note that flexible interconnection 403 is integrally formed with part of circuit board cells 402 and 404. Layer stack 400A may be used to construct circuit board cells that may have dense circuitry fabricated thereon. Circuit board cells constructed with layer stack 400A may be considered a rigid-flex circuit board cell.

FIG. 4B illustrates the construction of a circuit board cell 406 using layer stack 400B. Circuit board cell 406 constructed with layer stack 400B may include cover layers 432 and 439; three signal layers 433, 435, and 438; two polyimide cores 434 and 437; and an adhesive layer 436 arranged as shown. Layer stack 400B may be used to construct circuit board cells that may not have dense circuitry fabricated thereon. Circuit board cells constructed with layer stack 400B may be considered a flex circuit board cell.

FIG. 4C illustrates the construction of a circuit board cell and/or flexible interconnection 40X using layer stack 400C. Circuit board cell/flexible interconnection 40X constructed with layer stack 400C may include a cover layer 442; three signal layers 443, 445, and 448; two polyimide cores 444 and 447; an adhesive layer 446; cover layer portions 449A and 449B; an appropriately positioned adhesive layer 450; and an appropriately positioned stiffener layer 452 arranged as shown. Adhesive layer 450 and stiffener layer 452 may be appropriately positioned anywhere along the bottom of layer stack 400C such that support is provided to circuitry fabricated above, which may be dense. Layer stack 400C may therefore be used to construct circuit board cells and/or flexible interconnections that may have a portion thereof with dense circuitry fabricated thereon, while the remaining portion of the circuit board cell or flexible interconnection will not have dense circuitry (if any) fabricated thereon.

Any suitable materials may be used to construct layer stacks 400A, 400B, and 400C. For example, the cover layers may be a polyimide material, such as, e.g., Kapton®. The rigid and stiffener layers may be made using FR4, which is a rigid glass-reinforced epoxy resin laminate. Other possible materials may include fiber-reinforced laminates, UV cured resin, and thermoplastics. Kapton® may be used to form the polyimide cores. Any suitable acrylic adhesive may be used to form the adhesive layers. And the signal layers may be formed using copper, although other suitable conductive materials may be used.

In some embodiments, circuit board cell 406 may have an overall height or thickness ranging from 6.5 to 7.0 mils (0.165 to 0.18 mm). The use of a rigid or stiffener layer may add an additional 6.5 to 7.0 mils (0.165 to 0.18 mm) to the overall height or thickness of the circuit board cell. In some embodiments, the overall height of a CAM device constructed with circuit board cells and flexible interconnections described herein and enclosed in a housing may be about 2.5 mm (+/−5%) (as measured perpendicularly from, e.g., a user's skin surface with the CAM device attached thereto).

Figure 5:
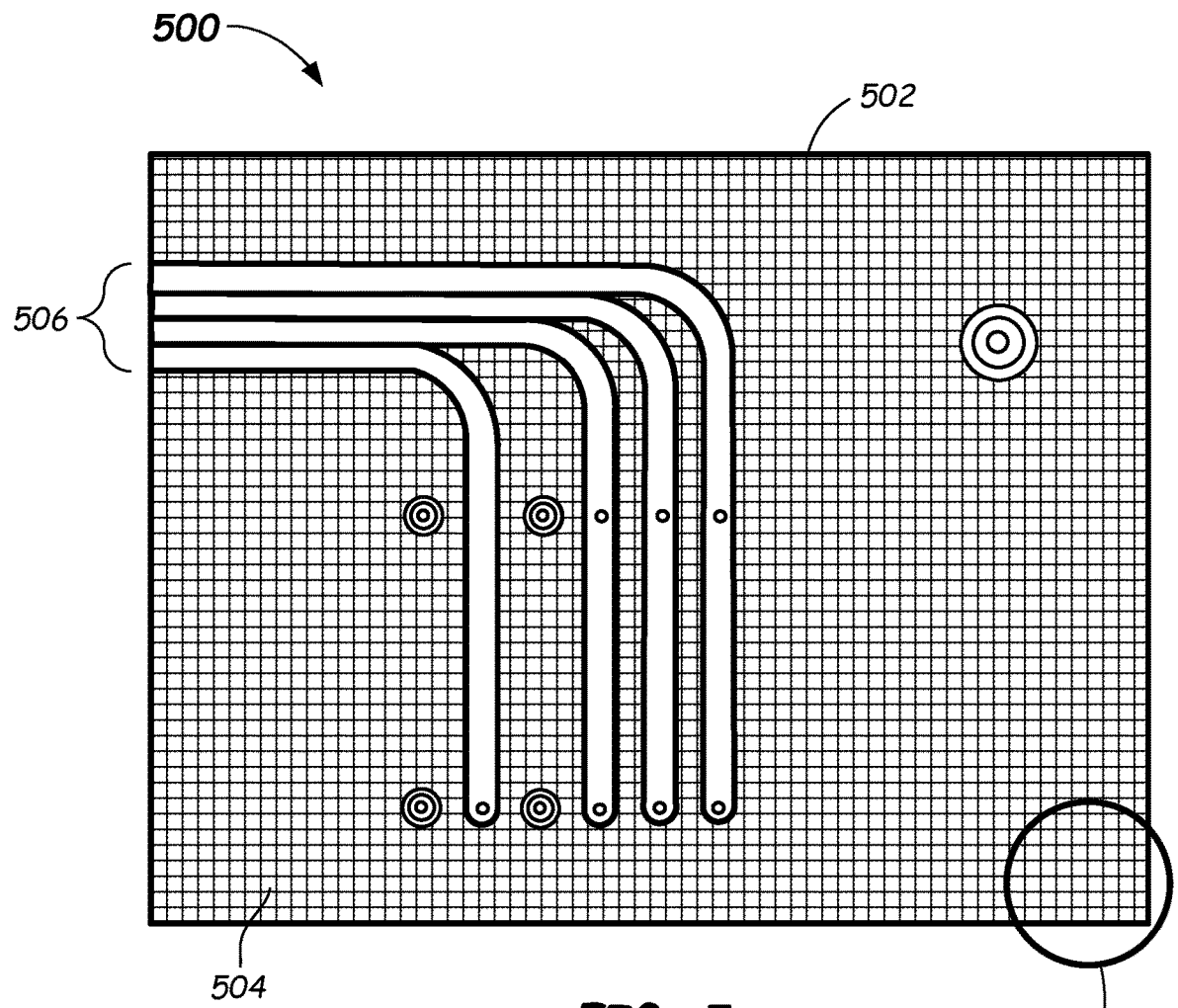
FIG. 5 illustrates a plan view of a hatched ground plane of a flexible circuit board.
Figure 5A:
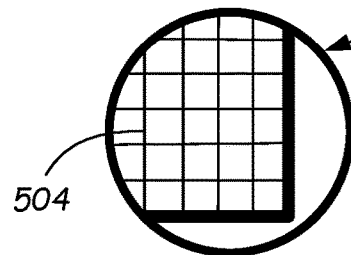
FIG. 5A illustrates an enlarged portion of the hatched ground plane of FIG. 5, according to embodiments provided herein.

FIG. 5 illustrates a portion 500 of a signal layer 502 of a circuit board cell having a hatched ground plane 504 according to one or more embodiments. Hatched ground plane 504 may extend over areas not occupied by signal lines 506 and may be on each signal layer of a circuit board cell. Hatched ground plane 504 may be copper, but other suitable conductor materials may alternatively be used. Hatched ground plane 504 has a mesh or net-like structure, as better shown in the enlarged view of FIG. 5A. The openings in hatched ground plane 504 may form generally square or rectangular shapes. Other suitable shapes may be possible. Hatched ground plane 504 increases the flexibility of a circuit board cell in comparison to conventional solid conductor ground planes, while maintaining the quality of RF (radio frequency) signals as would be conventionally provided by solid conductor ground planes.

Hatched ground plane 504 may be used on any one or more signal layers in layer stacks 400A-C (FIGS. 4A-C) and in any one or more circuit board cells and flexible interconnections of flexible circuit board configuration 200 (FIG. 2) and in any one or more of circuit board cells and flexible interconnections of flexible circuit board configuration 300 (FIG. 3).

Figure 6A:
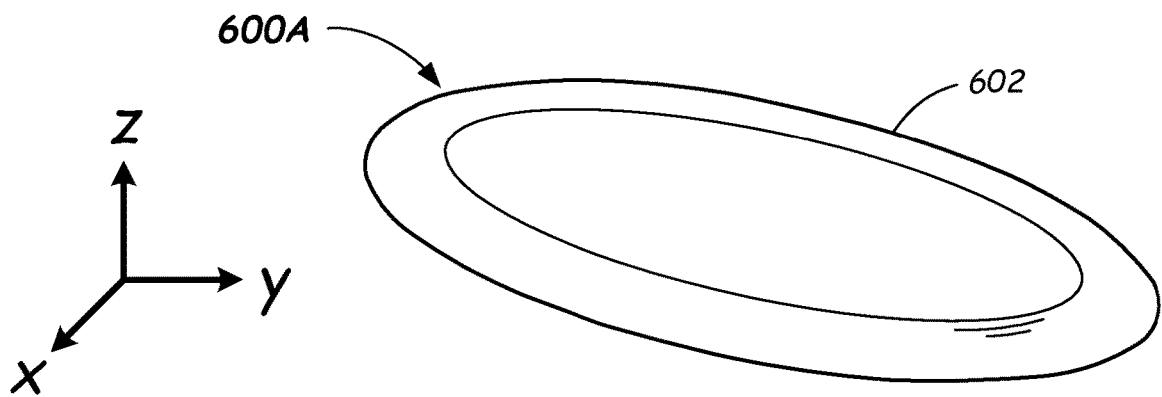
FIGS. 6A, 6B, and 6C illustrate perspective views of a continuous analyte monitoring (CAM) device having a flexible circuit board in an unflexed state, a flexed state about an X-axis dimension, and a flexed state about a Y-axis dimension, respectively, according to embodiments provided herein.
Figure 6B:
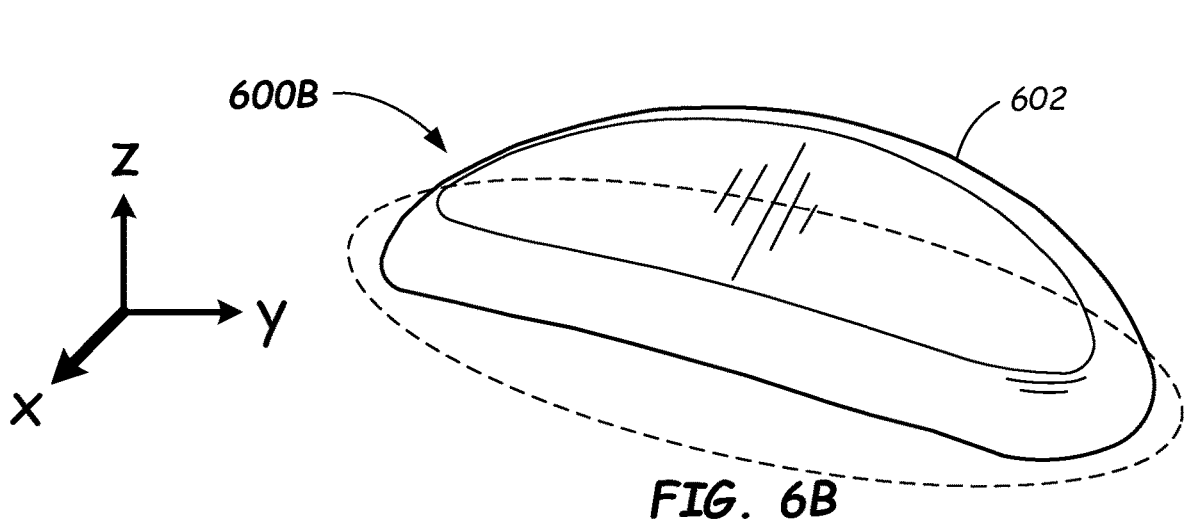
Figure 6C:
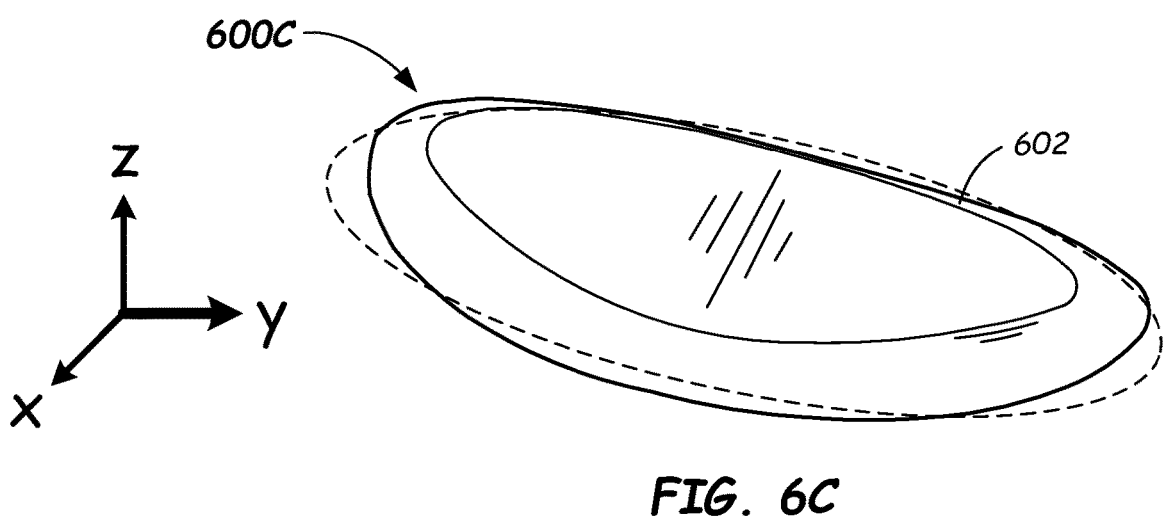

FIGS. 6A, 6B, and 6C illustrate unflexed and two flexed states, respectively, of a CAM device 602 built with a flexible circuit board (having, e.g., flexible circuit board configuration 200 or 300) according to one or more embodiments. In particular, FIG. 6A illustrates CAM device 602 in an unflexed state 600A. FIG. 6B illustrates CAM device 602 in a flexed state 600B, wherein CAM device 602 is flexed laterally in a direction along the X-axis dimension. And FIG. 6C illustrates CAM device 602 in a flexed state 600C, wherein CAM device 602 is flexed longitudinally in a direction along the Y-axis dimension. Advantageously, CAM device 600 may be flexible in directions other than those shown. For example, CAM device 600 may be flexible in any direction in three dimensions (e.g., the X-Y-Z plane as shown) having varying degrees of concurrent lateral and longitudinal flexing in both the X and Y axis dimensions.

Figure 7:
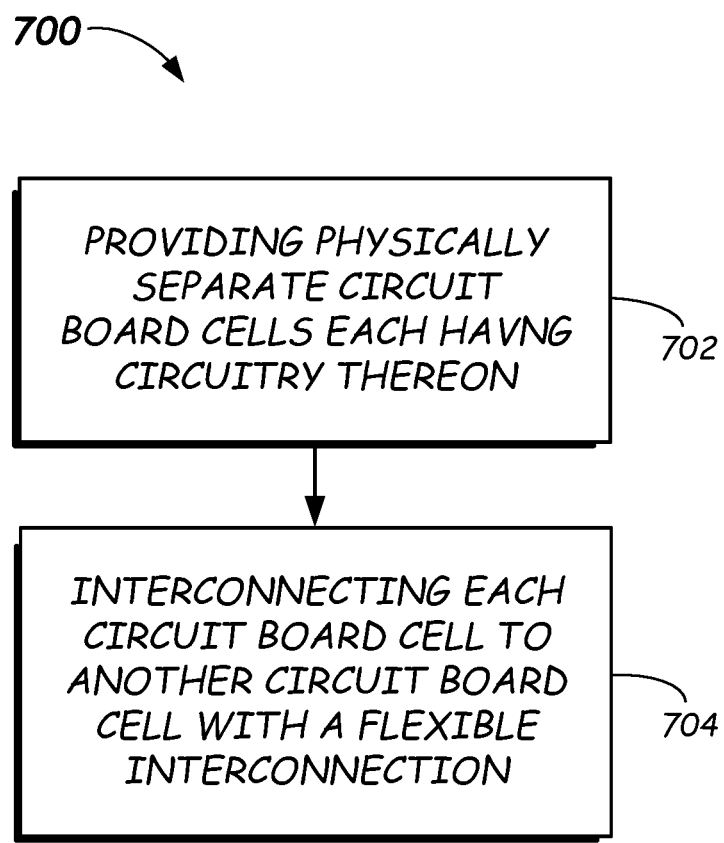
FIG. 7 illustrates a flowchart of a method of constructing a flexible circuit board according to embodiments provided herein.

FIG. 7 illustrates a method 700 of constructing a flexible circuit board for a CAM device according to one or more embodiments. At process block 702, method 700 may provide a plurality of physically separate circuit board cells each having circuitry thereon. For example, the physically separate circuit board cells may be, e.g., circuit board cells 202, 204, and/or 206 of FIGS. 2A-B or circuit board cells 302, 304, 306, and/or 308 of FIG. 3. The circuitry on the circuit board cells may include, e.g., CAM sensor circuitry, wireless communication circuitry, power circuitry, and/or interconnection circuitry, partitioned as shown in FIG. 3.

At process block 704, method 700 may include interconnecting each one of the plurality of physically separate circuit board cells to another of the plurality of physically separate circuit board cells with a respective flexible interconnection operable to couple power, electrical signals, or both to two interconnected circuit board cells. For example, as shown in FIGS. 2A-B and 3, each flexible interconnection may be any one of flexible interconnection 203, 205, 303, 305, 307, and/or 309. Note that the flexible interconnections are not detachable connectors configured to be removable and reconnectable, but instead, the flexible interconnections are fixedly and/or permanently attached to and/or integrally formed with the circuit board cells to form an integrated highly flexible circuit board configuration.

Note that in some embodiments, method 700 may include process blocks (not shown) that enclose within a housing configured to be attached to a skin surface of a user the plurality of physically separate circuit board cells each interconnected to another of the plurality of physically separate circuit board cells with a flexible interconnection.

Also note that in some embodiments, method 700 may include process blocks (not shown) that provide at least one of the physically separate circuit board cells with a hatched ground plane, and/or that construct at least one of the physically separate circuit board cells according to one of layer stacks 400A-C (FIGS. 4A-C).

While this disclosure is susceptible to various modifications and alternative forms, specific method and apparatus embodiments have been shown by way of example in the drawings and are described in detail herein. It should be understood, however, that the particular methods and apparatus disclosed herein are not intended to limit the disclosure or the claims.

What is claimed is:

1. A flexible circuit board for a continuous analyte monitoring (CAM) device, comprising:
   a plurality of physically separate circuit board cells each having circuitry thereon; and
   a plurality of flexible interconnections each connecting one of the plurality of physically separate circuit board cells to another of the plurality of physically separate circuit board cells, each one of the plurality of flexible interconnections operable to couple power, electrical signals, or both to physically separate circuit board cells connected thereto;
   wherein the flexible circuit board is bendable in multiple directions in three dimensions,
   wherein the flexible circuit board is communicatively coupled to at least one subcutaneous analyte sensor of the CAM device such that an analyte signal indicative of an analyte level of a user is received from the at least one analyte sensor by one of the plurality of physically separate circuit board cells.

2. The flexible circuit board of claim 1, wherein at least one of the plurality of physically separate circuit board cells comprises three signal layers, wherein two of the three signal layers are integrally formed with one of the plurality of flexible interconnections.

3. The flexible circuit board of claim 1, wherein at least one of the plurality of physically separate circuit board cells comprises a hatched ground plane.

4. The flexible circuit board of claim 1, wherein one of the plurality of flexible interconnections comprises circuitry fabricated thereon and a stiffener applied thereto to support the circuitry.

5. The flexible circuit board of claim 1, wherein one of the plurality of physically separate circuit board cells comprises CAM sensor circuitry associated with the at least one subcutaneous analyte sensor.

6. The flexible circuit board of claim 1, wherein one of the plurality of physically separate circuit board cells comprises wireless communication circuitry.

7. The flexible circuit board of claim 1, wherein one of the plurality of physically separate circuit board cells comprises power circuitry and a power source.

8. The flexible circuit board of claim 1, wherein one of the plurality of physically separate circuit board cells comprises interconnection circuitry.

9. The flexible circuit board of claim 1, wherein the CAM device is a continuous glucose monitoring device.

10. A continuous analyte monitoring (CAM) device comprising:
    the flexible circuit board of claim 1; and
    a housing configured to be attached to a skin surface of the user, the housing enclosing the flexible circuit board of claim 1;
    wherein the CAM device has a height measured from the skin surface of about 2.5 mm.

11. A method of constructing a flexible circuit board for a continuous analyte monitoring (CAM) device, the method comprising:

provagide a plurality of physically separate circuit board cells each having circuitry thereon; and interconnecting each one of the plurality of physically separate circuit board cells to another of the plurality of physically separate circuit board cells with a respective flexible interconnection operable to couple power, electrical signals, or both to the one and the another of the plurality of physically separate circuit board cells, wherein the flexible circuit board is communicatively coupled to at least one subcutaneous analyte sensor of the CAM device such that an analyte signal indicative of an analyte level of a user is received from the at least one analyte sensor by one of the plurality of physically separate circuit board cells.

12. The method of claim 11, further comprising enclosing within a housing configured to be attached to a skin surface of the user the plurality of physically separate circuit board cells each interconnected to another of the plurality of physically separate circuit board cells with the respective flexible interconnection.

13. The method of claim 11, further comprising constructing at least one of the plurality of physically separate circuit board cells to comprise three signal layers, wherein two of the three signal layers are integrally formed with one of the respective flexible interconnections.

14. The method of claim 11, further comprising providing at least one of the plurality of physically separate circuit board cells with a hatched ground plane.

15. The method of claim 11 further comprising fabricating circuitry on one of the respective flexible interconnections and applying a stiffener to support the circuitry.

16. The method of claim 11 further comprising fabricating CAM sensor circuitry on one of the plurality of physically separate circuit board cells wherein the CAM sensor circuitry is associated with the at least one subcutaneous analyte sensor.

17. The method of claim 11 further comprising fabricating wireless communication circuitry on one of the plurality of physically separate circuit board cells.

18. The method of claim 11 further comprising fabricating power circuitry and a power source on one of the plurality of physically separate circuit board cells.

19. The method of claim 11 further comprising fabricating interconnection circuitry on one of the plurality of physically separate circuit board cells.

20. The method of claim 11 wherein the CAM device is a continuous glucose monitoring device having a height of about 2.5 mm.

* * * * *